US010321980B2

(12) United States Patent
Ritzberger et al.

(10) Patent No.: US 10,321,980 B2
(45) Date of Patent: Jun. 18, 2019

(54) LITHIUM SILICATE GLASS CERAMIC AND GLASS WITH TRIVALENT METAL OXIDE

(71) Applicant: Ivoclar Vivadent AG, Schaan (LI)

(72) Inventors: Christian Ritzberger, Grabs (CH); Elke Apel, Oberschan (CH); Wolfram Höland, Schaan (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/193,202

(22) Filed: Jun. 27, 2016

(65) Prior Publication Data

US 2016/0302897 A1    Oct. 20, 2016

Related U.S. Application Data

(63) Continuation of application No. 14/001,184, filed as application No. PCT/EP2012/070221 on Oct. 11, 2012, now Pat. No. 9,402,699.

(30) Foreign Application Priority Data

Oct. 14, 2011  (EP) .................................... 11185336

(51) Int. Cl.

| C03C 8/00 | (2006.01) |
|---|---|
| A61C 13/083 | (2006.01) |
| C03C 3/095 | (2006.01) |
| C03C 3/097 | (2006.01) |
| C03C 4/00 | (2006.01) |
| C03C 10/00 | (2006.01) |
| A61C 13/20 | (2006.01) |
| A61C 13/00 | (2006.01) |
| C03B 19/06 | (2006.01) |
| C03C 19/00 | (2006.01) |
| C03C 23/00 | (2006.01) |

(52) U.S. Cl.
CPC ........ *A61C 13/083* (2013.01); *A61C 13/0022* (2013.01); *A61C 13/20* (2013.01); *C03B 19/063* (2013.01); *C03C 3/095* (2013.01); *C03C 3/097* (2013.01); *C03C 4/0021* (2013.01); *C03C 10/00* (2013.01); *C03C 10/0027* (2013.01); *C03C 19/00* (2013.01); *C03C 23/007* (2013.01); *C03C 2204/00* (2013.01)

(58) Field of Classification Search
CPC ............ C03C 10/0009; C03C 10/0018; C03C 10/0027
USPC .................................................. 501/2, 3, 4, 5
See application file for complete search history.

(56) References Cited

U.S. PATENT DOCUMENTS

| 2,684,911 A | 7/1954 | Stookey |
| 3,006,775 A | 10/1961 | Chen |
| 3,022,180 A | 2/1962 | Morrissey et al. |
| 3,161,528 A | 12/1964 | Eppler |
| 3,252,778 A | 5/1966 | Goodman et al. |
| 3,463,647 A | 8/1969 | Kosiorek |
| 3,804,608 A | 4/1974 | Gaskell et al. |
| 3,816,704 A | 6/1974 | Borom et al. |
| 3,977,857 A | 8/1976 | Mattox |
| 4,155,888 A | 5/1979 | Mooth |
| 4,189,325 A | 2/1980 | Barrett et al. |
| 4,414,282 A | 11/1983 | McCollister et al. |
| 4,473,653 A | 9/1984 | Rudoi |
| 4,480,044 A | 10/1984 | McAlinn |
| 4,515,634 A | 5/1985 | Wu et al. |
| 4,671,770 A | 6/1987 | Bell et al. |
| 4,963,707 A | 10/1990 | Zyokou et al. |
| 4,977,114 A | 12/1990 | Horinouchi et al. |
| 5,176,961 A | 1/1993 | Crooker et al. |
| 5,219,799 A | 6/1993 | Beall et al. |
| 5,432,130 A | 7/1995 | Rheinberger et al. |
| 5,507,981 A | 4/1996 | Petticrew et al. |
| 5,618,763 A | 4/1997 | Frank et al. |
| 5,628,564 A | 5/1997 | Nenyei et al. |
| 5,691,256 A | 11/1997 | Taguchi et al. |
| 5,698,019 A | 12/1997 | Frank et al. |
| 5,698,482 A | 12/1997 | Frank et al. |
| 5,702,514 A | 12/1997 | Petticrew |
| 5,707,777 A | 1/1998 | Aoai et al. |
| 5,872,069 A | 2/1999 | Abe |
| 5,874,376 A | 2/1999 | Taguchi et al. |
| 5,925,180 A | 7/1999 | Frank et al. |
| 5,938,959 A | 8/1999 | Wang |
| 5,968,856 A | 10/1999 | Schweiger et al. |
| 6,066,584 A | 5/2000 | Krell et al. |
| 6,095,682 A | 8/2000 | Hollander et al. |
| 6,106,747 A | 8/2000 | Wohlwend |

(Continued)

FOREIGN PATENT DOCUMENTS

| CA | 2163792 A1 | 12/1994 |
| CA | 2213390 | 3/1998 |

(Continued)

OTHER PUBLICATIONS

Jakovac, M., et al., Measurement of ion elution from dental ceramics, Journal of the European Ceramic Society, May 6, 2006, vol. 26, pp. 1695-1700.

(Continued)

Primary Examiner — Noah S Wiese
(74) Attorney, Agent, or Firm — Ann M. Knab; Thad McMurray

(57) ABSTRACT

Lithium silicate glass ceramics and glasses comprising specific oxides of trivalent elements are described which crystallize at low temperatures and are suitable in particular as dental materials.

23 Claims, No Drawings

(56) References Cited

U.S. PATENT DOCUMENTS

| | | | |
|---|---|---|---|
| 6,121,175 A | 9/2000 | Drescher et al. | |
| 6,048,589 A | 11/2000 | Suzuki | |
| 6,157,004 A | 12/2000 | Bizzio | |
| 6,163,020 A | 12/2000 | Bartusch et al. | |
| 6,174,827 B1 | 1/2001 | Goto et al. | |
| 6,252,202 B1 | 6/2001 | Zychek | |
| 6,267,595 B1 | 7/2001 | Gratz | |
| 6,270,876 B1 | 8/2001 | Abe et al. | |
| 6,287,121 B1 | 9/2001 | Guiot et al. | |
| 6,342,458 B1 | 1/2002 | Schweiger et al. | |
| 6,376,397 B1 | 4/2002 | Petticrew | |
| 6,420,288 B2 | 7/2002 | Clausbruch et al. | |
| 6,441,346 B1 | 8/2002 | Zychek | |
| 6,455,451 B1* | 9/2002 | Brodkin | A61K 6/033 106/35 |
| 6,458,728 B1 | 10/2002 | Nagata et al. | |
| 6,485,849 B2 | 11/2002 | Petticrew | |
| 6,514,890 B1 | 2/2003 | Nagata et al. | |
| 6,514,893 B1 | 2/2003 | Schweiger et al. | |
| 6,517,623 B1 | 2/2003 | Brodkin et al. | |
| 6,524,982 B1 | 2/2003 | Nagata et al. | |
| 6,593,257 B1 | 7/2003 | Nagata et al. | |
| 6,703,332 B2* | 3/2004 | Peng | C03C 10/0027 428/846.9 |
| 6,802,894 B2 | 10/2004 | Brodkin et al. | |
| 6,818,573 B2 | 11/2004 | Petticrew | |
| 7,162,321 B2 | 1/2007 | Luthardt et al. | |
| 7,316,740 B2 | 1/2008 | Rheinberger et al. | |
| 7,452,836 B2 | 11/2008 | Apel et al. | |
| 7,655,586 B1 | 2/2010 | Brodkin et al. | |
| 7,806,694 B2 | 10/2010 | Brodkin et al. | |
| 7,816,291 B2 | 10/2010 | Schweiger et al. | |
| 7,867,930 B2 | 1/2011 | Apel et al. | |
| 7,867,933 B2 | 1/2011 | Apel et al. | |
| 7,871,948 B2 | 1/2011 | Apel et al. | |
| 7,892,995 B2 | 2/2011 | Castillo | |
| 7,993,137 B2 | 8/2011 | Apel et al. | |
| 8,042,358 B2 | 10/2011 | Schweiger et al. | |
| 8,047,021 B2 | 11/2011 | Schweiger et al. | |
| 8,444,756 B2 | 5/2013 | Schweiger et al. | |
| 2001/0006174 A1 | 7/2001 | Brennan | |
| 2001/0031446 A1 | 10/2001 | Petticrew | |
| 2002/0009600 A1 | 1/2002 | Peng et al. | |
| 2002/0010063 A1 | 1/2002 | Schweiger et al. | |
| 2002/0022563 A1 | 2/2002 | Schweiger et al. | |
| 2002/0031670 A1 | 3/2002 | Goto et al. | |
| 2002/0035025 A1 | 3/2002 | Schweiger et al. | |
| 2002/0160694 A1 | 10/2002 | Wood et al. | |
| 2004/0182538 A1 | 9/2004 | Lambrecht | |
| 2005/0098064 A1 | 5/2005 | Schweiger et al. | |
| 2005/0127544 A1* | 6/2005 | Brodkin | A61C 13/26 264/16 |
| 2006/0040142 A1 | 2/2006 | Xuelu et al. | |
| 2006/0082033 A1 | 4/2006 | Hauptmann et al. | |
| 2006/0139091 A1 | 6/2006 | Fratti | |
| 2006/0257823 A1 | 11/2006 | Pfeiffer et al. | |
| 2006/0257824 A1 | 11/2006 | Pfeiffer et al. | |
| 2007/0023971 A1 | 2/2007 | Saha et al. | |
| 2007/0042889 A1 | 2/2007 | Apel et al. | |
| 2008/0044488 A1 | 2/2008 | Zimmer et al. | |
| 2008/0120994 A1 | 5/2008 | Schweiger et al. | |
| 2008/0199823 A1 | 8/2008 | Miller | |
| 2009/0023574 A1 | 1/2009 | Holand et al. | |
| 2009/0038344 A1 | 2/2009 | Apel et al. | |
| 2009/0038508 A1 | 2/2009 | Apel et al. | |
| 2009/0042166 A1 | 2/2009 | Craig et al. | |
| 2009/0256274 A1 | 10/2009 | Castillo | |
| 2009/0258778 A1 | 10/2009 | Castillo | |
| 2010/0083706 A1 | 4/2010 | Castillo | |
| 2011/0030423 A1 | 2/2011 | Johannes et al. | |
| 2011/0256409 A1 | 10/2011 | Ritzberger et al. | |
| 2012/0094822 A1 | 4/2012 | Castillo et al. | |
| 2012/0148988 A1 | 6/2012 | Castillo et al. | |
| 2012/0248642 A1 | 10/2012 | Ritzberger et al. | |
| 2012/0309607 A1 | 12/2012 | Durschang et al. | |
| 2014/0141960 A1 | 5/2014 | Borczuch-Laczka et al. | |

FOREIGN PATENT DOCUMENTS

| | | |
|---|---|---|
| CA | 2239865 | 12/1998 |
| CA | 2239869 | 12/1998 |
| CA | 2252660 | 5/1999 |
| CA | 2351154 | 12/2001 |
| DE | 2451121 | 5/1975 |
| DE | 4303458 C1 | 1/1994 |
| DE | 4314817 | 11/1994 |
| DE | 4423793 | 2/1996 |
| DE | 4423794 | 2/1996 |
| DE | 4428839 | 2/1996 |
| DE | 19647739 | 3/1998 |
| DE | 19725553 | 12/1998 |
| DE | 19725555 | 12/1998 |
| DE | 10031431 | 1/2002 |
| DE | 102007011337 | 9/2008 |
| EP | 231773 | 8/1987 |
| EP | 0827941 | 3/1998 |
| EP | 0916625 | 5/1999 |
| EP | 1152641 A1 | 11/2001 |
| EP | 1505041 | 2/2005 |
| EP | 1577275 | 2/2006 |
| EP | 1688398 | 8/2006 |
| GB | 752243 A | 7/1956 |
| GB | 2284655 A | 6/1995 |
| JP | H10323354 A | 12/1998 |
| JP | 1174418 | 3/1999 |
| JP | 2001019485 A | 1/2001 |
| JP | 2001019486 A | 1/2001 |
| JP | 2001019487 A | 1/2001 |
| JP | 2001019488 A | 1/2001 |
| JP | 2005-062832 A | 3/2005 |
| WO | 2007028787 A1 | 3/2007 |
| WO | 2008106958 | 9/2008 |
| WO | 2009126317 | 10/2009 |
| WO | 2011076422 | 6/2011 |

OTHER PUBLICATIONS

Apel, E., et al., "Influence of ZrO2 on the crystallization and properties of lithium disilicate glass-ceramics derived from multicomponent system," Journal of European Ceramic Society, 2007, 27, 1571-1577.

Durschang, Dr. Bernhard, "Report of Results," Fraunhofer Institute for Silicate Research ISC Glass and Mineral Materials, 2015.

McMillan, P.W., et al., "The Structure and Properties of a Lithium Zinc Silicate Glass-Ceramic," Journal of Material Science 1966, I. 269-279.

Deubener, J., et al., "Induction time analysis of nucleation and crystal grown in di- and metasilicate glasses," Journal of Non-Crystalline Solids, 1993, 163, 1-12.

Holand, W., et al., "Glass-ceramic technology," American Chemical Society 2002, Westerville OH, USA.

Holand, W., et al., "Control of nucleation in glass ceramics," Phil. Trans. Soc. Lond. A 2003, 361, 575-589.

Holand, W., et al., "Principles and phenomena of bioengineering with glass-ceramics of dental restoration," Journal of the European Ceramics Society 2007, 27, 1571-1577.

Ivoclar Vivadent, Inc., IPS e.max lithium disilicate, 627329, Rev. Feb. 2009.

Borom, M.P., et al., "Strength and Microstructure in Lithium Disilicate Glass Ceramics," J. Am. Ceram. Soc., 1975, 68, 385-391.

Stookey, S.D., "Chemical Machining of Photosensitive Glass," Ind. Eng. Chem. 45:115-118 (1993).

Von Clausbruch, et al., "Effect of ZnO on the Crystallization, Microstructure, and Properties of Glass-Ceramics in the SiO2—Li2O—K2O—P2O5 System," Glastech. Ber. Glass Sci. Technol. 74(8)223-229(2001).

Von Clausbruch, et al., "Effect of P2O5 on the Crystallization and Microstructure of Glass-Ceramics in the SiO2—Li2O—Zn)—P2O5 System," Glastech. Ber. Glass Sci. Technol. 74(8)223-229(2001).

(56) References Cited

OTHER PUBLICATIONS

Oliveria et al., "Sintering and Crystallization of a Glass Powder in the Li2O—ZrO2—SiO2 System," J. Amer. Ceramic Soc. 81(3): 777-780 (1998).
Giassi, et al., "Injection Moulding of LiO2—ZrO2—SiO2—A12O3 (LZSA) Glass Ceramics," Glass Technol., 46(3), 277-280 (2005).
http://en.wikipedia.org/wiki/Nucleation; Sep. 20, 2012.
International Agency for Research on Cancer (IARC) Working Group, "Arsenic and Arsenic Compounds," IARC Monographs; Arsenic, Metals, Fibres, and Dusts, vol. 100C, pp. 41-39, 2012.
International Agency for Research on Cancer (IARC) Working Group, "Antimony Trioxide and Antimony Trisulfide," IARC Monographs on the Evaluation of Carcinogenic Risks to Humans, vol. 47, pp. 291-305, 1989.
Montedo, et al., "Low Thermal Expansion Sintered LZSA Glass Ceramics," American Ceramic Society Bulletin, vol. 87, No. 7, pp. 34-40, Jul. 2008.

\* cited by examiner

LITHIUM SILICATE GLASS CERAMIC AND GLASS WITH TRIVALENT METAL OXIDE

CROSS-REFERENCE TO RELATED APPLICATIONS

This application is a continuation application of U.S. application Ser. No. 14/001,184, filed Aug. 23, 2013, which is the National Stage filing of International patent application PCT/EP2012/070221, filed on Oct. 11, 2012, which claims priority to European patent application No. 11185336.2 filed on Oct. 14, 2011, the disclosures of which are incorporated herein by reference in their entirety.

TECHNICAL FIELD

The invention relates to lithium silicate glass ceramic and glass which comprise trivalent metal oxide selected from $Y_2O_3$, $La_2O_3$, $Yb_2O_3$, $Bi_2O_3$ and mixtures thereof and are particularly suitable for use in dentistry, preferably for the preparation of dental restorations.

BACKGROUND OF THE INVENTION

Lithium silicate glass ceramics are characterized as a rule by very good mechanical properties, which is why they have been used for a long time in the dental field and there primarily for the preparation of dental crowns and small bridges. The known lithium silicate glass ceramics usually contain as main components $SiO_2$, $Li_2O$, $Na_2O$ or $K_2O$, and nucleating agents such as $P_2O_5$.

DE 24 51 121 describes lithium disilicate glass ceramics which contain $K_2O$ and $Al_2O_3$. They are prepared from corresponding nuclei-containing starting glasses which are heated to temperatures of from 850 to 870° C. for the crystallization of lithium disilicate.

EP 827 941 describes sinterable lithium disilicate glass ceramics for dental purposes, which also contain $K_2O$ or $Na_2O$ in addition to $La_2O_3$. The lithium disilicate crystal phase is produced at a temperature of 850° C.

Lithium disilicate glass ceramics which also contain $La_2O_3$ and $K_2O$ are known from EP 916 625. A heat treatment is carried out at 870° C. for the formation of lithium disilicate.

EP 1 505 041 describes lithium silicate glass ceramics containing $K_2O$, which, when lithium metasilicate is present as main crystal phase, can be very satisfactorily mechanically processed e.g. by means of CAD/CAM processes, in order to then be converted by further heat treatment at temperatures of from 830 to 850° C. into high-strength lithium disilicate glass ceramics.

EP 1 688 398 describes similar $K_2O$— and $Al_2O_3$-containing lithium silicate glass ceramics which additionally are substantially free from ZnO. A heat treatment at 830 to 880° C. is applied to them to produce lithium disilicate.

U.S. Pat. No. 5,507,981 describes processes for producing dental restorations and glass ceramics that can be used in these processes. These are in particular lithium disilicate glass ceramics which usually contain $Na_2O$ or $K_2O$.

U.S. Pat. No. 6,455,451 relates to lithium disilicate glass ceramics which also contain $K_2O$. However, the production of the desired lithium disilicate crystal phase requires high temperatures of from 800 to 1000° C.

WO 2008/106958 discloses lithium disilicate glass ceramics for veneering zirconium oxide ceramics. The glass ceramics contain $Na_2O$ and are produced by heat treatment of nuclei-containing glasses at 800 to 940° C.

WO 2009/126317 describes $GeO_2$-containing lithium metasilicate glass ceramics which also comprise $K_2O$. The glass ceramics are processed to form dental products primarily by machining.

WO 2011/076422 relates to lithium disilicate glass ceramics which also contain $K_2O$ in addition to high levels of $ZrO_2$ or $HfO_2$. The crystallization of lithium disilicate takes place at temperatures of from 800 to 1040° C.

The known lithium disilicate glass ceramics have in common that they require heat treatments at more than 800° C. in order to effect the precipitation of lithium disilicate as main crystal phase. A large quantity of energy is therefore necessary to prepare them. Further, in the known glass ceramics the alkali metal oxides $K_2O$ or $Na_2O$ as well as $ZrO_2$ are as a rule present as essential components which are apparently required for the production of the glass ceramics with the desired properties and in particular the formation of the desired lithium disilicate main crystal phase.

SUMMARY OF THE INVENTION

There is therefore a need for lithium silicate glass ceramics during the preparation of which the crystallization of lithium disilicate can be effected at lower temperatures. Further, it should also be possible to prepare them without the alkali metal oxides $K_2O$ or $Na_2O$ as well as $ZrO_2$, previously regarded as necessary, and they should be suitable in particular for the preparation of dental restorations primarily in view of their optical and mechanical properties.

This object is achieved by the dental lithium silicate glass ceramic according to the attached claims. Also a subject of the invention are the dental starting glass, the dental lithium silicate glass with nuclei, the process for the preparation of the dental glass ceramic and the dental lithium silicate glass with nuclei according to the attached claims.

DETAILED DESCRIPTION OF THE INVENTION

The lithium silicate glass ceramic according to the invention is characterized in that it comprises trivalent metal oxide selected from $Y_2O_3$, $La_2O_3$, $Yb_2O_3$, $Bi_2O_3$ and mixtures thereof, wherein the glass ceramic is essentially free $K_2O$ and $Na_2O$.

The trivalent metal oxide is preferably selected from $Y_2O_3$, $Yb_2O_3$, $Bi_2O_3$ and mixtures thereof.

It is preferred that the glass ceramic comprises the trivalent metal oxide or mixtures thereof in an amount of 0.1 to 15, in particular 2.0 to 10.0, preferably 2.0 to 8.0 and particularly preferably 2.4 to 6.0 wt.-%.

It is particularly surprising that the formation of the glass ceramic according to the invention with lithium disilicate as main crystal phase is achieved even in the absence of various components regarded as necessary for conventional glass ceramics, such as in particular $K_2O$ and $Na_2O$, and even at very low and thus advantageous crystallization temperatures of in particular 630 to 720° C. The glass ceramic also has a combination of optical and mechanical properties as well as processing properties that are very advantageous for use as dental material.

Further, a glass ceramic is preferred which comprises less than 0.1 wt.-% MgO and ZnO. The glass ceramic is particularly preferably essentially free of MgO and ZnO.

A glass ceramic is also preferred, which excludes lithium silicate glass ceramic comprising at least 6.1 wt.-% $ZrO_2$.

Further, a glass ceramic is also preferred, which excludes lithium silicate glass ceramic comprising at least 8.5 wt.-% transition metal oxide selected from the group consisting of oxides of yttrium, oxides of transition metals with an atomic number of 41 to 79 and mixtures of these oxides.

The glass ceramic according to the invention preferably comprises 55.0 to 85.0, in particular 60.0 to 80.0 and preferably 66.0 to 78.0 wt.-% $SiO_2$.

It is also preferred that the glass ceramic comprises 13.0 to 21.0 and in particular 13.0 to 20.0 and particularly preferably 15.0 to 18.0 wt.-% $Li_2O$.

It is further preferred that the molar ratio between $SiO_2$ and $Li_2O$ is from 1.7 to 3.1 and in particular from 1.8 to 3.0. It is very surprising that the production of lithium disilicate is achieved within this broad range. Specifically at ratios of less than 2.0 customary materials form lithium metasilicate instead of lithium disilicate.

The glass ceramic according to the invention can also comprise nucleating agents. $P_2O_5$ is particularly preferably used for this. The glass ceramic preferably comprises 0 to 8.0, in particular 2.0 to 8.0, preferably 2.5 to 6.0 and particularly preferably 3.0 to 5.0 wt.-% $P_2O_5$.

In a further preferred embodiment, the glass ceramic comprises at least one and preferably all of the following components:

| Component | wt.-% |
|---|---|
| $SiO_2$ | 68.0 to 78.0 |
| $Li_2O$ | 13.0 to 20.0 |
| trivalent metal oxide and mixtures thereof | 2.0 to 6.0 |
| $Al_2O_3$ | 0 to 6.0 |
| $Rb_2O$ and/or $Cs_2O$ | 0 to 5.0 |
| $P_2O_5$ | 0 to 4.5, preferably 3.0 to 4.5. |

The glass ceramic according to the invention can moreover also comprise additional components which are selected in particular from oxides of divalent elements, further oxides of tetravalent elements, further oxides of pentavalent elements, oxides of hexavalent elements, melt accelerators, colourants and fluorescent agents.

In particular the alkaline earth metal oxides, preferably CaO, BaO, MgO, SrO or a mixture thereof and preferably MgO and/or CaO come into consideration as oxides of divalent elements. They can be used in amounts of 0 to 5.0 wt.-%.

The term "further oxides of tetravalent elements" refers to oxides of tetravalent elements with the exception of $SiO_2$. Examples of suitable further oxides of tetravalent elements are $TiO_2$, $SnO_2$ and $GeO_2$.

The term "further oxides of pentavalent elements" refers to oxides of pentavalent elements with the exception of $P_2O_5$.

Examples of suitable further oxides of pentavalent elements are $Ta_2O_5$ and $Nb_2O_5$.

Examples of suitable oxides of hexavalent elements are $WO_3$ and $MoO_3$.

A glass ceramic is preferred which comprises at least one oxide of divalent elements, at least one further oxide of tetravalent elements, at least one further oxide of pentavalent elements and/or at least one oxide of hexavalent elements.

Examples of melt accelerators are fluorides.

Examples of colourants and fluorescent agents are oxides of d- and f-elements, such as the oxides of Ti, V, Sc, Mn, Fe, Co, Ta, W, Ce, Pr, Nd, Tb, Er, Dy, Gd, Eu and Yb. Metal colloids, e.g. of Ag, Au and Pd, can also be used as colourants and in addition can also act as nucleating agents. These metal colloids can be formed e.g. by reduction of corresponding oxides, chlorides or nitrates during the melting and crystallization processes. The metal colloids can be present in the glass ceramic in an amount of 0.005 to 0.5 wt.-%.

The term "main crystal phase" used below refers to the crystal phase which has the highest proportion by volume compared with other crystal phases.

In one embodiment, the glass ceramic according to the invention comprises lithium metasilicate as main crystal phase. In particular, the glass ceramic comprises more than 5 vol.-%, preferably more than 10 vol.-% and particularly preferably more than 15 vol.-% lithium metasilicate crystals, relative to the total glass ceramic.

In a further particularly preferred embodiment, the glass ceramic comprises lithium disilicate as main crystal phase. In particular the glass ceramic comprises more than 10 vol.-%, preferably more than 20 vol.-% and particularly preferably more than 30 vol.-% lithium disilicate crystals, relative to the total glass ceramic.

The lithium disilicate glass ceramic according to the invention is characterized by particularly good mechanical properties and can be produced e.g. by heat treatment of the lithium metasilicate glass ceramic according to the invention. However, it can be formed in particular by heat treatment of a corresponding starting glass or of a corresponding lithium silicate glass with nuclei.

It has surprisingly been shown that the lithium disilicate glass ceramic according to the invention has very good mechanical and optical properties and processing properties even in the absence of components regarded as essential for conventional glass ceramics. The combination of its properties even allows it to be used as dental material and in particular material for the preparation of dental restorations.

The lithium disilicate glass ceramic according to the invention has in particular a fracture toughness, measured as $K_{IC}$ value, of at least 1.8 MPa·m$^{0.5}$ and in particular at least 2.0 MPa·m$^{0.5}$.

This value was determined using the Vickers method and calculated using Niihara's equation.

The invention also relates to a lithium silicate glass with nuclei that are suitable for forming lithium metasilicate and/or lithium disilicate crystals, wherein the glass comprises the components of the above-described glass ceramics according to the invention. Thus this glass comprises trivalent metal oxide selected from $Y_2O_3$, $La_2O_3$, $Yb_2O_3$, $Bi_2O_3$ and mixtures thereof, wherein the glass is essentially free of $K_2O$ and $Na_2O$. For preferred embodiments of this glass reference is made to the preferred embodiments described above of the glass ceramics according to the invention.

The glass with nuclei according to the invention can be produced by heat treatment of a correspondingly composed starting glass according to the invention. The lithium metasilicate glass ceramic according to the invention can then be formed by a further heat treatment, and in turn be converted into the lithium disilicate glass ceramic according to the invention by further heat treatment, or the lithium disilicate glass ceramic according to the invention can also preferably be formed directly from the glass with nuclei. The starting glass, the glass with nuclei and the lithium metasilicate glass ceramic can consequently be regarded as precursors for the production of the high-strength lithium disilicate glass ceramic.

The glass ceramics according to the invention and the glasses according to the invention are present in particular in the form of powders, granulates or blanks, e.g. monolithic blanks, such as platelets, cuboids or cylinders, or powder compacts, in unsintered, partly sintered or dense-sintered form. They can easily be further processed in these forms. They can, however, also be present in the form of dental restorations, such as inlays, onlays, crowns, veneers, facets or abutments.

The invention also relates to a process for the preparation of the glass ceramic according to the invention and the glass with nuclei according to the invention, in which a correspondingly composed starting glass, the glass with nuclei according to the invention or the lithium metasilicate glass ceramic according to the invention is subjected to at least one heat treatment in the range of 450 to 950° C., in particular 450 to 750 and preferably 480 to 720° C.

The starting glass according to the invention therefore comprises trivalent metal oxide selected from $Y_2O_3$, $La_2O_3$, $Yb_2O_3$, $Bi_2O_3$ and mixtures thereof, wherein the starting glass is essentially free of $K_2O$ and $Na_2O$. In addition, it preferably also comprises suitable amounts of $SiO_2$ and $Li_2O$, in order to allow the formation of a lithium silicate glass ceramic, and in particular a lithium disilicate glass ceramic. Further, the starting glass can also comprise still further components, such as are given above for the lithium silicate glass ceramic according to the invention. All those embodiments are preferred for the starting glass which are also given as preferred for the glass ceramic.

In the process according to the invention, the glass with nuclei is usually prepared by means of a heat treatment of the starting glass at a temperature of in particular from 480 to 510° C. The lithium disilicate glass ceramic according to the invention is then preferably produced from the glass with nuclei through further heat treatment at usually 600 to 750 and in particular 630 to 720° C.

Thus, much lower temperatures are used according to the invention for the crystallization of lithium disilicate than with the conventional lithium disilicate glass ceramics. The energy thus saved represents a clear advantage. Surprisingly, this low crystallization temperature is even possible in the absence of components, such as $K_2O$ and $Na_2O$ as well as $ZrO_2$, regarded as essential for conventional glass ceramics.

To prepare the starting glass, the procedure is in particular that a mixture of suitable starting materials, such as carbonates, oxides, phosphates and fluorides, is melted at temperatures of in particular 1300 to 1600° C. for 2 to 10 h. To achieve a particularly high homogeneity, the obtained glass melt is poured into water in order to form a glass granulate, and the obtained granulate is then melted again.

The melt can then be poured into moulds to produce blanks of the starting glass, so-called solid glass blanks or monolithic blanks.

It is also possible to put the melt into water again in order to prepare a granulate. This granulate can then be pressed, after grinding and optionally addition of further components, such as colourants and fluorescent agents, to form a blank, a so-called powder compact.

Finally, the starting glass can also be processed to form a powder after granulation.

The starting glass, e.g. in the form of a solid glass blank, a powder compact or in the form of a powder, is then subjected to at least one heat treatment in the range of from 450 to 950° C. It is preferred that a first heat treatment is initially carried out at a temperature in the range of 480 to 510° C. to prepare a glass according to the invention with nuclei which are suitable for forming lithium metasilicate and/or lithium disilicate crystals. This first heat treatment is preferably carried out for a period of 10 min to 120 min and in particular 10 min to 30 min. The glass with nuclei can then preferably be subjected to at least one further heat treatment at a higher temperature and in particular more than 570° C. to effect crystallization of lithium metasilicate or lithium disilicate. This further heat treatment is preferably carried out for a period of 10 min to 120 min, in particular 10 min to 60 min and particularly preferably 10 min to 30 min. To crystallize lithium disilicate, the further heat treatment is usually carried out at 600 to 750 and in particular 630 to 720° C.

In a preferred embodiment of the process, therefore
(a) the starting glass is subjected to a heat treatment at a temperature of 480 to 510° C. in order to form the glass with nuclei, and
(b) the glass with nuclei is subjected to a heat treatment at a temperature of 630 to 720° C. in order to form the glass ceramic with lithium disilicate as main crystal phase.

The duration of the heat treatments carried out in (a) and (b) is preferably as given above.

The at least one heat treatment carried out in the process according to the invention can also take place during hot pressing or sintering-on of the glass according to the invention or the glass ceramic according to the invention.

Dental restorations for use in the oral cavity, such as bridges, inlays, onlays, crowns, veneers, facets or abutments, can be prepared from the glass ceramics according to the invention and the glasses according to the invention. The invention therefore also relates to their use for the preparation of dental restorations. It is preferred that the glass ceramic or the glass is shaped into the desired dental restoration by pressing or machining.

The pressing is usually carried out under increased pressure and increased temperature. It is preferred that the pressing is carried out at a temperature of 700 to 1200° C. It is further preferred to carry out the pressing at a pressure of 2 to 10 bar. During pressing, the desired shape change is achieved by viscous flow of the material used. The starting glass according to the invention and in particular the glass with nuclei according to the invention, the lithium metasilicate glass ceramic according to the invention and the lithium disilicate glass ceramic according to the invention can be used for the pressing. The glasses and glass ceramics according to the invention can be used in particular in the form of blanks, e.g. solid blanks or powder compacts.

The machining is usually carried out by material removal processes and in particular by milling and/or grinding. It is particularly preferred that the machining is carried out within the framework of a CAD/CAM process. The starting glass according to the invention, the glass with nuclei according to the invention, the lithium metasilicate glass ceramic according to the invention and the lithium disilicate glass ceramic according to the invention can be used for the machining. The glasses and glass ceramics according to the invention can be used in particular in the form of blanks, e.g. solid blanks or powder compacts, e.g. in unsintered, partly sintered or dense-sintered form. The lithium metasilicate glass ceramic according to the invention and lithium disilicate glass ceramic according to the invention are preferably used for the machining. The lithium disilicate glass ceramic can also be used in a not fully crystallized form which was produced by heat treatment at a lower temperature. This has the advantage that an easier machining, and thus the use of simpler equipment for the machining, is possible. After the machining of such a partly crystallized material, it is usually subjected to a heat treatment at a higher temperature and in particular 630 to 720° C. in order to effect further crystallization of lithium disilicate.

In general, after the preparation of the dental restoration shaped as desired by pressing or machining, it can also in particular be heat-treated in order to convert the precursors used, such as starting glass, glass with nuclei or lithium metasilicate glass ceramic, into lithium disilicate glass ceramic or to increase the crystallization of lithium disilicate or to reduce the porosity, e.g. of a porous powder compact used.

However, the glass ceramic according to the invention and the glass according to the invention are also suitable as coating material of e.g. ceramics and glass ceramics. The invention is therefore also directed towards the use of the glass according to the invention or the glass ceramic according to the invention for coating in particular ceramics and glass ceramics.

The invention also relates to a process for coating ceramics and glass ceramics, in which the glass ceramic according to the invention or the glass according to the invention is applied to the ceramic or glass ceramic and is exposed to increased temperature.

This can take place in particular by sintering-on and preferably by pressing-on. With sintering-on, the glass ceramic or the glass is applied to the material to be coated, such as ceramic or glass ceramic, in the usual way, e.g. as powder, and then sintered at increased temperature. With the preferred pressing-on, the glass ceramic according to the invention or the glass according to the invention is pressed on, e.g. in the form of powder compacts or monolithic blanks, at an increased temperature of e.g. 700 to 1200° C., applying pressure, e.g. 2 to 10 bar. The methods described in EP 231 773 and the press furnace disclosed therein can be used in particular for this. A suitable furnace is e.g. the Programat EP 5000 from Ivoclar Vivadent AG, Liechtenstein.

It is preferred that, after conclusion of the coating process, the glass ceramic according to the invention is present with lithium disilicate as main crystal phase, as such glass ceramic has particularly good properties.

Because of the above-described properties of the glass ceramic according to the invention and the glass according to the invention as its precursor, they are suitable in particular for use in dentistry. A subject of the invention is therefore also the use of the glass ceramic according to the invention or the glass according to the invention as a dental material and in particular for the preparation of dental restorations or as a coating material for dental restorations, such as crowns, bridges and abutments.

Finally, the glasses and glass ceramics according to the invention can also be mixed together with other glasses and glass ceramics in order to produce dental materials with properties set as desired. Compositions and in particular dental materials which comprise the glass according to the invention or the glass ceramic according to the invention in combination with at least one other glass and/or one other glass ceramic therefore represent a further subject of the invention. The glass according to the invention or the glass ceramic according to the invention can therefore be used in particular as main component of an inorganic-inorganic composite or in combination with a plurality of other glasses and/or glass ceramics, wherein the composites or combinations can be used in particular as dental materials. The combinations or composites can particularly preferably be present in the form of sintered blanks. Examples of other glasses and glass ceramics for the preparation of inorganic-inorganic composites and of combinations are disclosed in DE 43 14 817, DE 44 23 793, DE 44 23 794, DE 44 28 839, DE 196 47 739, DE 197 25 553, DE 197 25 555, DE 100 31 431 and DE 10 2007 011 337. These glasses and glass ceramics belong to the silicate, borate, phosphate or aluminosilicate group. Preferred glasses and glass ceramics are of $SiO_2$—$Al_2O_3$—$K_2O$ type (with cubic or tetragonal leucite crystals), $SiO_2$—$B_2O_3$—$Na_2O$ type, alkali-silicate type, alkali-zinc-silicate type, silicophosphate type, $SiO_2$—$ZrO_2$ type and/or lithium-aluminosilicate type (with spodumene crystals). By mixing such glasses or glass ceramics with the glasses and/or glass ceramics according to the invention, for example the coefficient of thermal expansion can be set as desired in a broad range of from 6 to $20 \cdot 10^{-6}$ $K^{-1}$.

The invention is explained in more detail below by means of examples.

EXAMPLES

Examples 1 to 15—Composition and Crystal Phases

A total of 15 glasses and glass ceramics according to the invention with the composition given in Table I were prepared by melting corresponding starting glasses followed by heat treatment for controlled nucleation and crystallization.

For this, the starting glasses weighing from 100 to 200 g were first melted from customary raw materials at 1400 to 1500° C., wherein the melting was very easily possible without formation of bubbles or streaks. By pouring the starting glasses into water, glass frits were prepared which were then melted a second time at 1450 to 1550° C. for 1 to 3 h for homogenization.

In the case of Examples 1 and 3 to 15, the obtained glass melts were then poured into preheated moulds in order to produce glass monoliths.

In the case of Example 2, the obtained glass melt was cooled to 1400° C. and converted to a finely divided granulate by pouring into water. The granulate was dried and ground to a powder with a particle size of <90 μm. This powder was moistened with some water and pressed to form a powder compact at a pressure of 20 MPa.

The glass monoliths (Examples 1 and 3-15) as well as the powder compact (Example 2) were then converted by thermal treatment to glasses and glass ceramics according to the invention. The thermal treatments used for controlled nucleation and controlled crystallization are also given in Table I. The following meanings apply $T_N$ and $t_N$ Temperature and time used for nucleation
$T_C$ and $t_C$ Temperature and time used for crystallization of lithium disilicate or lithium metasilicate It can be seen that a first heat treatment in the range of 480 to 510° C. resulted in the formation of lithium silicate glasses with nuclei and these glasses crystallized by a further heat treatment already at 630 to 720° C. within only 20 to 30 min to glass ceramics with lithium disilicate or lithium metasilicate as main crystal phase, as was established by X-ray diffraction tests.

The produced lithium silicate glass ceramics were able to be very satisfactorily machined in a CAD/CAM process or hot-pressed into the form of various dental restorations, which were also provided with a veneer if required.

They were also able to be applied by hot pressing as coatings onto in particular dental restorations, e.g. in order to veneer the latter as desired.

Example 16—Processing Via Powder Compacts

The glass ceramic according to Example 14 was ground to powder with an average particle size of <90 m.

In a first variant, the obtained powder was pressed with or without pressing auxiliaries to powder compacts and the latter were partly or densely sintered at temperatures of from 800 to 1100° C. and then further processed by machining or by hot pressing to form dental restorations.

In a second variant, the obtained powder was pressed with or without pressing auxiliaries to powder compacts and the latter were then further processed by machining or by hot pressing to form dental restorations. In particular, the dental restorations obtained after the machining were then densely sintered at temperatures of 900 to 1100° C.

With both variants, it was possible to prepare in particular crowns, caps, partial crowns and inlays as well as coatings on dental ceramics and dental glass ceramics.

Example 17—Hot Pressing of Glass with Nuclei

A glass with the composition according to Example 2 was prepared by mixing corresponding raw materials in the form of oxides and carbonates for 30 min in a Turbula mixer and then melting the mixture at 1450° C. for 120 min in a platinum crucible. The melt was poured into water in order to obtain a finely divided glass granulate. This glass granulate was melted again at 1530° C. for 150 min in order to obtain a glass melt with particularly high homogeneity. The temperature was reduced to 1500° C. for 30 min and cylindrical glass blanks with a diameter of 12.5 mm were prepared by pouring into pre-heated, separable steel moulds or graphite moulds. The obtained glass cylinders were then nucleated at 510° C. and stress-relieved.

The nucleated glass cylinders were then processed by hot pressing at a pressing temperature of 970° C. and a pressing time of 6 min using an EP600 press furnace, Ivoclar Vivadent AG, to form dental restorations, such as inlays, onlays, veneers, partial crowns, crowns, laminating materials and laminates. In each case, lithium disilicate was detected as main crystal phase.

TABLE I

| | Example | | | | | | |
|---|---|---|---|---|---|---|---|
| Composition | 1 wt.-% | 2 wt.-% | 3 wt.-% | 4 wt.-% | 5 wt.-% | 6 wt.-% | 7 wt.-% |
| $SiO_2$ | 72.5 | 75.8 | 66.0 | 77.4 | 71.2 | 68.5 | 73.8 |
| $Li_2O$ | 15.0 | 15.8 | 17.5 | 16.1 | 19.2 | 16.8 | 15.3 |
| $P_2O_5$ | 3.2 | — | 7.0 | 3.5 | 4.3 | 3.1 | 3.4 |
| $Al_2O_3$ | 3.3 | 3.0 | 3.4 | — | 2.7 | 2.5 | — |
| $Rb_2O$ | — | — | — | — | — | — | 4.5 |
| $Cs_2O$ | — | — | — | — | — | 3.6 | — |
| $Y_2O_3$ | 6.0 | 5.4 | 1.3 | — | — | — | 3.0 |
| $La_2O_3$ | — | — | — | — | 2.6 | 2.4 | — |
| $Yb_2O_3$ | — | — | 2.8 | 3.0 | — | 3.1 | — |
| $Bi_2O_3$ | — | — | — | — | — | — | — |
| MgO | — | — | 2.0 | — | — | — | — |
| CaO | — | — | — | — | — | — | — |
| $SiO_2/Li_2O$ Molar ratio | 2.4 | 2.4 | 1.9 | 2.4 | 1.8 | 2.0 | 2.4 |
| Optical properties (after pouring) | transparent | transparent | transparent | opaque glass | transparent | transparent | transparent |
| $T_g/°$ C. | 486 | 482 | 474 | 472 | 462 | 474 | 479 |
| $T_N/°$ C. | 480 | 510 | 480 | 490 | 500 | 500 | 500 |
| $t_N$/min. | 10 | 10 | 10 | 10 | 10 | 10 | 10 |
| $T_c/°$ C. | 700 | 700 | 670 | 630 | 700 | 700 | 700 |
| $t_c$/min. | 20 | 20 | 30 | 20 | 20 | 20 | 20 |
| Main crystal phase | Lithium disilicate | Lithium disilicate | Lithium metasilicate | Lithium disilicate | Lithium disilicate | Lithium disilicate | Lithium disilicate |
| Other crystal phases | Cristobalite, $Li_3PO_4$ | — | — | $Li_3PO_4$ | $Li_3PO_4$; $Li_2SiO_3$ | $Li_3PO_4$; $Li_2SiO_3$ | $Li_3PO_4$; $Li_2SiO_3$ |

| | Example | | | | | | | |
|---|---|---|---|---|---|---|---|---|
| Composition | 8 wt.-% | 9 wt.-% | 10 wt.-% | 11 wt.-% | 12 wt.-% | 13 wt.-% | 14 wt.-% | 15 wt.-% |
| $SiO_2$ | 73.8 | 73.8 | 76.9 | 73.3 | 75.4 | 72.3 | 77.4 | 73.3 |
| $Li_2O$ | 15.3 | 15.3 | 13.0 | 15.2 | 15.6 | 15.0 | 16.1 | 15.7 |
| $P_2O_5$ | 3.4 | 3.4 | 3.8 | 3.4 | 3.4 | 3.3 | 3.5 | 3.5 |
| $Al_2O_3$ | — | — | 3.3 | — | — | 3.4 | — | 3.5 |
| $Rb_2O$ | — | 2.0 | — | — | — | — | — | — |
| $Cs_2O$ | 4.5 | — | — | — | — | — | — | — |
| $Y_2O_3$ | 3.0 | 3.0 | 3.0 | 3.6 | 3.6 | 3.0 | 3.0 | — |
| $La_2O_3$ | — | — | — | — | — | 3.0 | — | — |
| $Yb_2O_3$ | — | — | — | — | — | — | — | — |
| $Bi_2O_3$ | — | — | — | — | — | — | — | 4.0 |
| MgO | — | 2.5 | — | — | — | — | — | — |
| CaO | — | — | — | 4.5 | 2.0 | — | — | — |
| $SiO_2/Li_2O$ Molar ratio | 2.4 | 2.4 | 2.94 | 2.4 | 2.4 | 2.4 | 2.4 | 2.3 |
| Optical properties (after pouring) | transparent | transparent | transparent | translucent, opalescent | translucent, opalescent | transparent | opaque glass | transparent |
| $T_g/°$ C. | 481 | 471 | 483 | 474 | 474 | 480 | 470 | 458 |
| $T_N/°$ C. | 500 | 500 | 500 | 500 | 500 | 500 | 490 | 480 |
| $t_N$/min. | 10 | 10 | 10 | 10 | 10 | 10 | 10 | 10 |

TABLE I-continued

| $T_c$/° C. | 700 | 700 | 700 | 700 | 700 | 700 | 650 | 720 |
|---|---|---|---|---|---|---|---|---|
| $t_c$/min. | 20 | 20 | 20 | 20 | 20 | 20 | 20 | 20 |
| Main crystal phase | Lithium disilicate | Lithium disilicate | Lithium disilicate | Lithium disilicate | Lithium disilicate | Lithium disilicate | Lithium disilicate | Lithium disilicate |
| Other crystal phases | $Li_3PO_4$ | $Li_3PO_4$ | $Li_3PO_4$ | $Li_3PO_4$ | $Li_3PO_4$ | $Li_3PO_4$ | $Li_3PO_4$ | $Li_3PO_4$ |

The invention claimed is:

1. Lithium silicate glass ceramic for the preparation of dental restorations for use in the oral cavity from said glass ceramic or for the coating of dental restorations for use in the oral cavity with said glass ceramic, wherein said glass ceramic comprises a trivalent metal oxide selected from $Y_2O_3$, $La_2O_3$, $Yb_2O_3$, $Bi_2O_3$ and mixtures thereof, wherein the glass ceramic is substantially free from $K_2O$ and $Na_2O$.

2. Glass ceramic according to claim 1, which comprises less than 0.1 wt.-% MgO and ZnO.

3. Glass ceramic according to claim 1, wherein the trivalent metal oxide is selected from $Y_2O_3$, $Yb_2O_3$, $Bi_2O_3$ and mixtures thereof.

4. Glass ceramic according to claim 1, which comprises the trivalent metal oxide or mixtures thereof in an amount of from 0.1 to 15 wt.-%.

5. Glass ceramic according to claim 1, which has lithium metasilicate as main crystal phase.

6. Glass ceramic according to claim 1, which has lithium disilicate as main crystal phase.

7. Glass ceramic according to claim 1, which comprises 55.0 to 85.0 wt.-% $SiO_2$.

8. Glass ceramic according to claim 1, which comprises 13.0 to 21.0 wt.-% $Li_2O$.

9. Glass ceramic according to claim 1, which comprises 0 to 8.0 wt.-% $P_2O_3$.

10. Glass ceramic according to claim 1, which comprises $SiO_2$ and $Li_2O$ in a molar ratio of from 1.7 to 3.1.

11. Glass ceramic according to claim 1, wherein lithium silicate glass ceramic is excluded which comprises at least 6.1 wt.-% $ZrO_2$.

12. Glass ceramic according to claim 1, wherein lithium silicate glass ceramic is excluded which comprises at least 8.5 wt.-% transition metal oxide selected from the group consisting of oxides of yttrium, oxides of transition metals with an atomic number from 41 to 79 and mixtures of these oxides.

13. Glass ceramic according to claim 1, which comprises at least one of the following components:

| Component | wt.-% |
|---|---|
| $SiO_2$ | 68.0 to 78.0 |
| $Li_2O$ | 13.0 to 20.0 |
| trivalent metal oxide and mixtures thereof | 2.0 to 6.0 |
| $Al_2O_3$ | 0 to 6.0 |
| $Rb_2O$ and/or $Cs_2O$ | 0 to 5.0 |
| $P_2O_5$ | 0 to 4.5. |

14. Lithium silicate glass ceramic according to claim 1, which has lithium disilicate as main crystal phase and a fracture toughness, measured as $K_{IC}$ value, of at least 1.8 $MPa \cdot m^{0.5}$.

15. Glass ceramic according to claim 1, wherein the glass ceramic is present in the form of a powder, a granular material, a blank or a dental restoration.

16. Dental lithium silicate glass with nuclei which are suitable for forming lithium metasilicate and/or lithium disilicate crystals, wherein the glass comprises the components of the glass ceramic according to claim 1.

17. Glass according to claim 16, wherein the glass ceramic is present in the form of a powder, a granular material, a blank or a dental restoration.

18. Process for the preparation of the glass ceramic according to claim 1, wherein a starting glass, a glass with nuclei or a glass ceramic with lithium metasilicate as main crystal phase is subjected to at least one heat treatment in the range of from 450 to 950° C.

19. Process for the preparation of the glass according to claim 17, wherein a starting glass is subjected to at least one heat treatment in the range of from 450 to 950° C.

20. Process for the preparation of a lithium silicate glass ceramic which comprises a trivalent metal oxide selected from $Y_2O_3$, $La_2O_3$, $Yb_2O_3$, $Bi_2O_3$ and mixtures thereof, wherein the glass ceramic is substantially free from $K_2O$ and $Na_2O$, wherein
   (a) a starting glass which comprises the components of the glass ceramic is subjected to a heat treatment for a period of 10 min to 30 min at a temperature of from 480 to 510° C. in order to form a glass with nuclei which are suitable for forming lithium disilicate crystals, and
   (b) the glass with nuclei is subjected to a heat treatment at a temperature of from 630 to 720° C. for a period of 10 min to 60 min in order to form a glass ceramic with lithium disilicate as main crystal phase.

21. Process of using a lithium silicate glass ceramic, a starting glass or a glass with nuclei which are suitable for forming lithium metasilicate and/or lithium disilicate crystals, wherein the glass ceramic and the glass comprise a trivalent metal oxide selected from $Y_2O_3$, $La_2O_3$, $Yb_2O_3$, $Bi_2O_3$ and mixtures thereof and is substantially free from $K_2O$ and $Na_2O$, as a dental material comprising preparing a dental restoration for use in the oral cavity from said glass ceramic or coating a dental restoration for use in the oral cavity with said glass ceramic.

22. Process according to claim 21, wherein preparing the dental restoration comprises shaping by pressing or machining the glass ceramic or the glass to the dental restoration.

23. Process according to claim 20, wherein the heat treatment of step (b) is for a period of from 10 min to 30 min.

* * * * *